United States Patent
Stastka et al.

(10) Patent No.: US 12,004,981 B2
(45) Date of Patent: Jun. 11, 2024

(54) SYSTEMS AND METHODS FOR ON-DEVICE CONSTRAINING MECHANISM CONSTRUCTION

(71) Applicant: W. L. Gore & Associates, Inc., Newark, DE (US)

(72) Inventors: Jerry J. Stastka, Flagstaff, AZ (US); Tyson J. Skelton, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 460 days.

(21) Appl. No.: 17/251,485

(22) PCT Filed: Jun. 14, 2018

(86) PCT No.: PCT/US2018/037582
§ 371 (c)(1),
(2) Date: Dec. 11, 2020

(87) PCT Pub. No.: WO2019/240799
PCT Pub. Date: Dec. 19, 2019

(65) Prior Publication Data
US 2021/0251788 A1    Aug. 19, 2021

(51) Int. Cl.
*A61F 2/95*        (2013.01)
*D04C 3/48*       (2006.01)

(52) U.S. Cl.
CPC .............. *A61F 2/9525* (2020.05); *D04C 3/48* (2013.01); *A61F 2002/9511* (2013.01)

(58) Field of Classification Search
CPC ............. D04C 3/48; A61F 2/95; A61F 2/9525
See application file for complete search history.

(56) References Cited

U.S. PATENT DOCUMENTS

| | | | | |
|---|---|---|---|---|
| 4,519,290 A | * | 5/1985 | Inman | F02K 9/97 87/9 |
| 4,878,906 A | | 11/1989 | Lindemann et al. | |
| 5,320,696 A | * | 6/1994 | McConnell | B29C 53/845 87/9 |
| 5,405,378 A | | 4/1995 | Strecker | |
| 5,693,089 A | * | 12/1997 | Inoue | A61F 2/95 606/198 |

(Continued)

FOREIGN PATENT DOCUMENTS

| | | |
|---|---|---|
| JP | 2006-051080 A | 2/2006 |
| JP | 2006-510453 A | 3/2006 |

(Continued)

OTHER PUBLICATIONS

International Search Report and Written Opinion received for PCT Patent Application No. PCT/US2018/037582, dated Mar. 8, 2019, 8 pages.

*Primary Examiner* — Shaun R Hurley (57) ABSTRACT

Various aspects of the present disclosure are directed apparatuses, systems and methods that include forming a constraining mechanism for an implantable medical device delivery. The apparatuses, systems and methods may include reducing a diameter of the implantable medical from a deployed diameter to a reduced diameter and interlocking one or more fibers along a length of the implantable medical device while the implantable medical device is in the reduced diameter to form the constraining mechanism.

18 Claims, 6 Drawing Sheets

(56) References Cited

U.S. PATENT DOCUMENTS

| | | | |
|---|---|---|---|
| 6,096,027 A * | 8/2000 | Layne | A61F 2/958 606/1 |
| 6,146,416 A | 11/2000 | Andersen et al. | |
| 6,224,627 B1 | 5/2001 | Armstrong et al. | |
| 6,315,792 B1 | 11/2001 | Armstrong et al. | |
| 6,702,845 B1 | 3/2004 | Cully et al. | |
| 9,622,893 B2 | 4/2017 | Huser | |
| 2004/0122503 A1* | 6/2004 | Campbell | A61F 2/97 623/1.12 |
| 2007/0038310 A1 | 2/2007 | Guetty | |
| 2009/0000264 A1* | 1/2009 | Ueda | D04B 1/22 57/328 |

FOREIGN PATENT DOCUMENTS

| | | |
|---|---|---|
| JP | 2021-526429 A | 10/2021 |
| WO | 99/65420 A1 | 12/1999 |
| WO | 2004/058047 A2 | 7/2004 |
| WO | 2019/240799 A1 | 12/2019 |

* cited by examiner

SYSTEMS AND METHODS FOR ON-DEVICE CONSTRAINING MECHANISM CONSTRUCTION

CROSS-REFERENCE TO RELATED APPLICATION

This application is a U.S. 371 Application of International Application PCT/US2018/037582, filed Jun. 14, 2018, which is herein incorporated by reference in its entirety for all purposes.

FIELD

The present disclosure relates to apparatuses, systems, and methods that include constructing coverings used in delivery of implantable medical devices. More specifically, the present disclosure relates to apparatuses, systems, and methods that include constructing coverings for constraining an expandable device during device delivery.

BACKGROUND

Stents and stent-grafts may be utilized to radially support a variety of tubular passages in the body, including arteries, veins, airways, gastrointestinal tracts, and biliary tracts. The preferred method of placing these devices has been to use specialized delivery systems to precisely place and deploy a device at the site to be treated. These delivery systems allow the practitioner to minimize the trauma and technical difficulties associated with device placements. Attributes of delivery systems include: low profile; ability to pass through introducer sheaths; ability to negotiate tortuous vasculature, smoothly and atraumatically; protection of constrained devices; and ability to accurately position and deploy the device.

Stents or stent-grafts may be deployed and plastically deformed by using an inflatable balloon (e.g., balloon expandable stents) or to self-expand and elastically recover (e.g., "self expandable" stents) from a collapsed or constrained delivery diameter to an expanded and deployed diameter. Some stents are designed to elastically recover by being manufactured at their functional diameter out of a material that has elastic recovery properties, and then radially compressed to be mounted on a delivery catheter.

These stent and stent-graft devices may be held, compressed, or constrained in the delivery configuration prior to and during delivery to a target location. The devices may be held in this compressed state for a prolonged period of time (e.g., after manufacture and prior to use). Different mechanisms or devices may be used to hold the stent and stent-graft devices in a delivery state and be removed to allow expansion of the stent and stent-graft devices at the target location.

SUMMARY

According to one example ("Example 1"), a method of forming a constraining mechanism for an implantable medical device delivery includes reducing a diameter of the implantable medical device from a deployed diameter to a reduced diameter; wrapping one or more fibers circumferentially about the implantable medical device; and interlocking the one or more fibers along a length of the implantable medical device while the implantable medical device is in the reduced diameter to form the constraining mechanism.

According to another example ("Example 2"), further to Example 1, interlocking the one or more fibers along the length of the implantable medical device includes braiding the one or more fibers to form the constraining mechanism.

According to another example ("Example 3"), further to any one of Examples 1-2, interlocking the one or more fibers along the length of the implantable medical device includes forming knots by knitting the one or more fibers.

According to another example ("Example 4"), further to any one of Examples 1-3, interlocking the one or more fibers includes knitting the one or more fibers together while the one or more fibers are in direct contact with the implantable medical device.

According to another example ("Example 5"), further to any one of Examples 1-4, reducing the diameter of the implantable medical device includes forcing the implantable medical device through a funnel having internal surfaces reducing in diameter.

According to another example ("Example 6"), further to Example 5, interlocking the one or more fibers includes arranging the one or more fibers along the implantable medical device as the implantable medical device exits the funnel in the reduced diameter.

According to another example ("Example 7"), further to any one of Examples 5-6, the funnel includes internal surfaces reducing an internal diameter of the funnel and a braiding zone having a length approximately equal to a length of the implantable medical device.

According to another example ("Example 8"), further to any one of Examples 5-7, the method further includes arranging the one or more fibers about an external surface of the funnel, and dragging the one or more fibers along the external surface of the funnel toward an end of the funnel where the implantable medical device exits the funnel in the reduced diameter to engage the implantable medical device.

According to another example ("Example 9"), further to any one of Examples 1-7, interlocking the one or more fibers occurs along the length of the implantable medical device in a first direction to form a first layer of the constraining mechanism, and further comprising interlocking the one or more fibers back onto the first layer along the length of the implantable medical device in a second direction to form a second layer of the constraining mechanism.

According to another example ("Example 10"), further to any one of Examples 1-8, interlocking the one or more fibers includes using a braider to knit together the one or more fibers.

According to another example ("Example 11"), further to Example 9, wherein the braider includes one or more needles, and the one or more needles are equal to the one or more fibers, and interlocking the one or more fibers includes knitting together the one or more fibers by the one or more needles.

According to one Example ("Example 12"), a system for forming a constraining mechanism for an implantable medical device delivery includes a funnel configured to reduce a diameter of the implantable medical device from a deployed diameter to a reduced diameter; and a braider configured to interlock one or more fibers along a length of the implantable medical device while the implantable medical device is in the reduced diameter to form the constraining mechanism.

According to another Example ("Example 13"), further to Example 12, the funnel includes internal surfaces reducing an internal diameter of the funnel and a braiding zone having a length approximately equal to a length of the implantable medical device.

According to another example ("Example 14"), further to any one of Examples 12-13, the braider includes one or more needles, and the one or more needles are equal to the one or more fibers, and interlocking the one or more fibers includes knitting together the one or more fibers by the one or more needles.

According to another example ("Example 15"), further to any one of Examples 12-14, the funnel is configured to facilitate arrangement of the one or more fibers on the implantable medical device for interlocking of the one or more fibers.

According to one Example ("Example 16"), a method includes loading an implantable medical device into a funnel having internal surfaces reducing an internal diameter of the funnel and a braiding zone; reducing a diameter of the implantable medical device by forcing the implantable medical device through the internal surfaces reducing the internal diameter of the funnel; and applying one or more fibers to the implantable medical device as the implantable medical device exits the braiding zone of the funnel to maintain the implantable medical device at reduced diameter.

According to another Example ("Example 17"), further to Example 16, applying the one or more fibers includes knotting a single fiber together to form a constraining mechanism.

According to another Example ("Example 18"), further to Example 16, applying the one or more fibers includes knitting together two or more fibers to form a constraining mechanism.

According to another Example ("Example 19"), further to Example 16, the method includes arranging the one or more fibers about an external surface of the funnel, and dragging the one or more fibers along the external surface of the funnel toward an end of the funnel where the implantable medical device exits the funnel in the reduced diameter to engage the implantable medical device.

According to another Example ("Example 20"), further to Example 16, applying one or more fibers includes interlocking the one or more fibers occurs along the length of the implantable medical device in a first direction to form a first layer of the constraining mechanism, and further comprising interlocking the one or more fibers back onto the first layer along the length of the implantable medical device in a second direction to form a second layer of the constraining mechanism.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

The accompanying drawings are included to provide a further understanding of the disclosure and are incorporated in and constitute a part of this specification, illustrate embodiments, and together with the description serve to explain the principles of the disclosure.

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed toward apparatuses, systems, and methods that include forming or manufacturing a constraining mechanism. The constraining mechanisms are configured to hold, compress, or constrain an implantable medical device (e.g., a stent, stent-graft, balloon, or other expandable medical device) in a delivery configuration prior to and during delivery to a target location. In certain instances, the constraining mechanism includes one or more fibers.

The constraining mechanisms, in accordance with the various aspects of the present disclosure, may be formed or manufactured directly on the implantable medical device. The fiber or fibers are knit, sewn, or interlocked to form the constraining mechanisms. Thus, the fiber or fibers are knit, sewn, or interlocked together about or around the implantable medical device. As noted above, the implantable medical devices are reduced, collapsed, or constrained to a reduced (delivery) diameter by the constraining mechanism for delivery into a target location into a patient where it is deployed or expanded to a deployed diameter (larger than the reduced diameter). As a result, and in certain instances, the fiber or fibers are interlocked, knit or sewn on the implantable medical device while the device is in the reduced (delivery) diameter.

Certain prior constraining mechanisms that use fibers are knit or interlocked prior to being applied to or arranged about an implantable medical device. The prior constraining mechanisms are formed as a separate component and added as a separate step in a manufacturing process. Compared to these prior constraining mechanisms, for example, the processing steps are reduced by way of forming the fiber constraining mechanism directly on the implantable medical device. Eliminating a step in the process may decrease the opportunity for errors or failures in the loading process such as improper constraining mechanism arrangement or damage to the implantable medical device (e.g., bent stent struts, broken stent struts, fiber tangles, improper constraining mechanism length such as fiber length, improper layering of the fiber).

Figure 1:
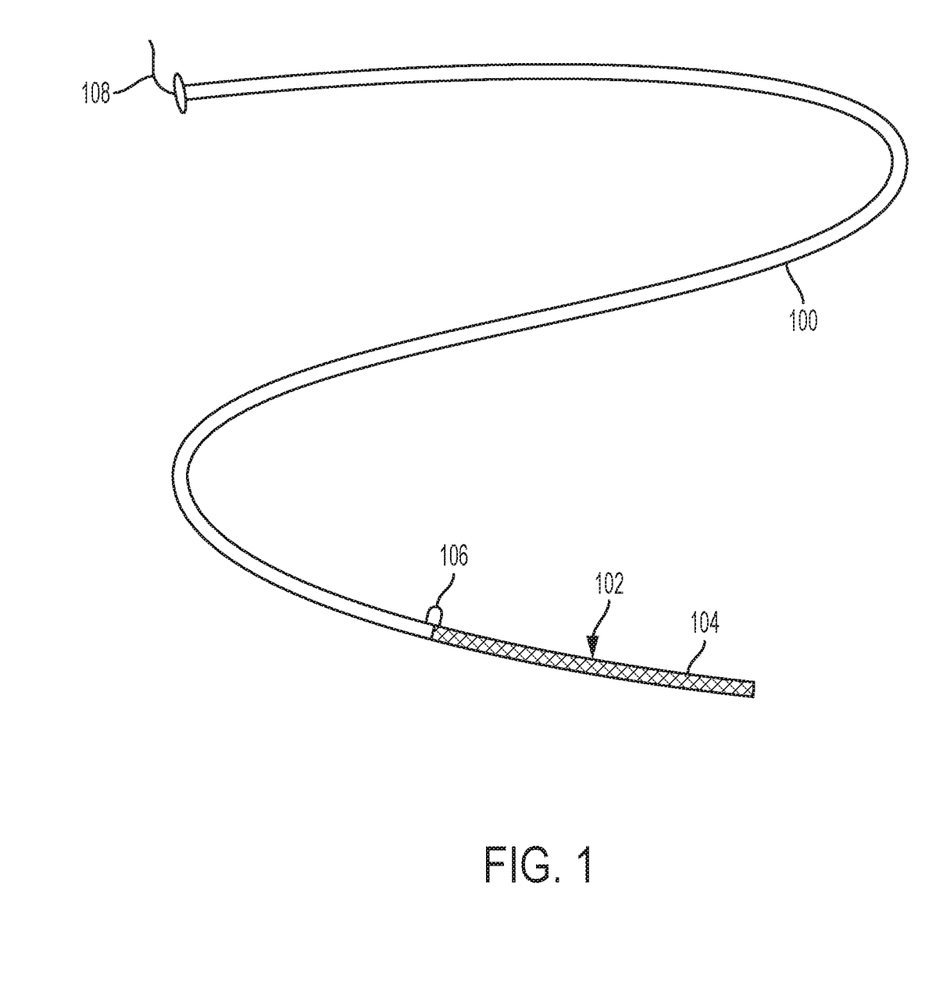
FIG. 1 is a top plan view of a catheter with a constraining mechanism, according to some embodiments.

FIG. 1 is a top plan view of a catheter 100 with a constraining mechanism 102, according to some embodiments. As shown in FIG. 1, the constraining mechanism 102 is configured to constrain an expandable medical device 104 to a delivery configuration. The constraining mechanism 102 may include one or more fibers 106 arranged about the expandable medical device 104 to maintain the constraining mechanism 102 in a constrained configuration.

The constraining mechanism 102 is arranged along a length of the expandable medical device 104. The constraining mechanism 102 is also circumferentially arranged about the expandable medical device 104 and may substantially cover the expandable medical device 104 for delivery. The one or more fibers 106 may be arranged within a lumen (not shown) of the catheter 100 and extend toward a proximal end of the catheter 100 that is arranged external to a patient during delivery of the expandable medical device 104. The one or more fibers 106 include a proximal end 108 that a user may apply tension to in order to release the constraining mechanism 102 and deploy the expandable medical device 104.

In certain instances, the one or more fibers 106 release similar to a rip cord such that interlocking portions (e.g., overlapping fibers or knots) sequentially release along the length of the expandable medical device 104. As is explained in greater detail below, the constraining mechanism 102 is formed by interlocking together the one or more fibers 106 directly on the expandable medical device 104. As compared to prior multiple fiber constraining mechanisms which are knitted together and then subsequently arranged about a constrained device, the constraining mechanism 102 is formed directly on the expandable medical device 104. The expandable medical device 104 may be a stent, stent-graft, a balloon, or a similar device.

Figure 2A:
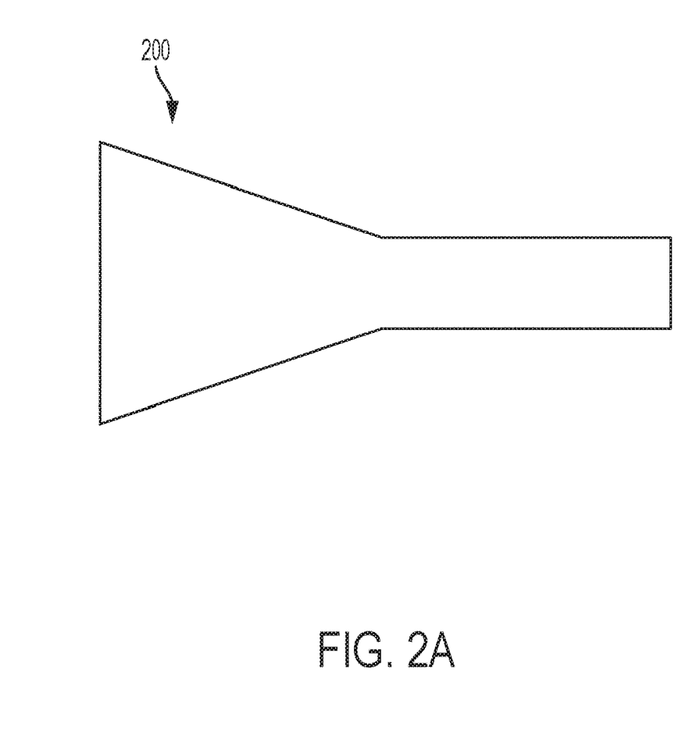
FIG. 2A is a side view of an example funnel for reducing an implantable medical device to a reduced diameter according to some embodiments.
Figure 2B:
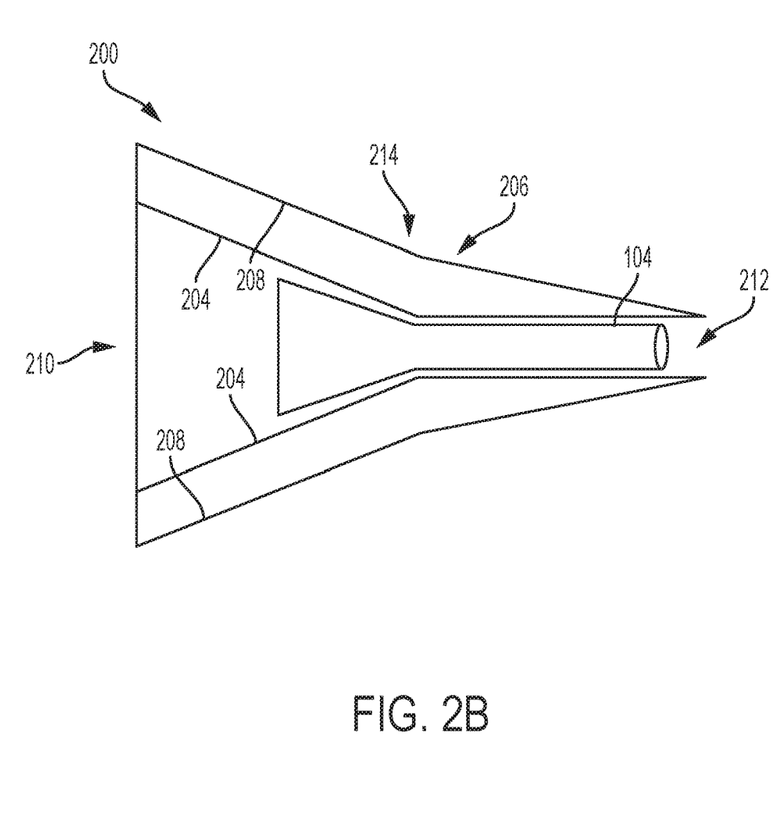
FIG. 2B is a partial cutaway view of the funnel shown in FIG. 2A.
Figure 3A:
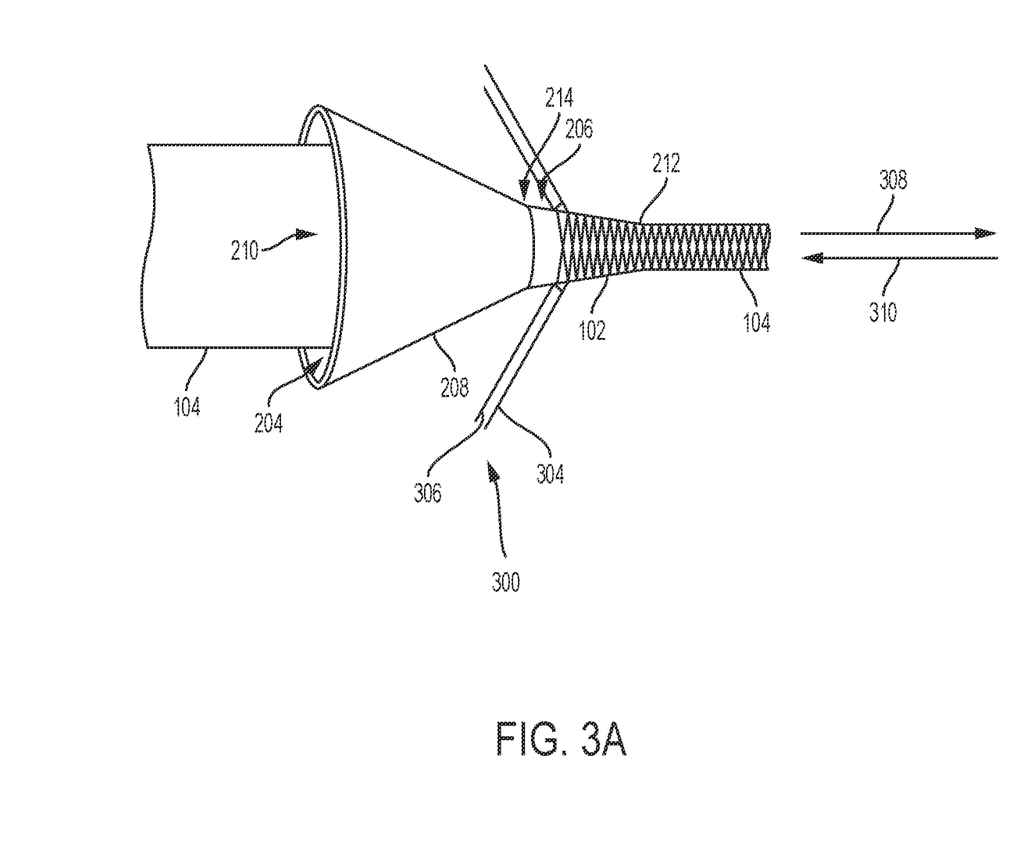
FIG. 3A is an example braider and implantable medical device according to some embodiments.

FIG. 2A is an example funnel 200 for reducing an implantable medical device 104 to a reduced diameter according to some embodiments. The funnel 200 is configured to reduce a diameter of an implantable medical device 104 from a deployed (or expanded) diameter to a reduced diameter. As shown in FIG. 2B, the funnel 200 includes internal surfaces 204 reducing an internal diameter of the funnel 200 and a braiding zone 206. The implantable medical device 104 is shown with portions in an expanded diameter (between the internal surfaces 204 reducing an internal diameter of the funnel 200) and at a reduced diameter (between internal surfaces of the braiding zone 206). The braiding zone 206 is described as the landing point for the one or more fibers 304 when forming the constraining mechanism 102 and may consist of an extension of the funnel 200 as shown in FIG. 3A. The braiding zone 206 may also consist only of the constrained device 104 as it passes the exit point 212 of the funnel 200. The braiding zone can be different lengths, for example, 20%, 30%, 40%, 50%, 60%, 70%, 80%, 90%, 100%, 110%, 120%, 130%, 140%, 150% of the implantable medical device length or any length between.

In certain instances, the internal surfaces 204 of the funnel 200 that reduce in diameter may be tapered. In addition, the tapered internal surfaces 204 lead directly into the braiding zone 206 of the funnel 200. Internal surfaces 204 of the braiding zone 206 of the funnel 200 may be substantially linear. The implantable medical device 104 may be loaded into an entry point 210 of the funnel 200. When loaded through the entry point 210 of and into the funnel 200, the tapered internal surfaces 204 forced the implantable medical device 104 to a constrained configuration in which the implantable medical device 104 has a reduced diameter. The implantable medical device 104 has a reduced diameter through the braiding zone 206 of the funnel 200 and is forced out an exit point 212 of the funnel 200.

As shown in FIGS. 2A-B, external surfaces 208 of the funnel 200 include a similar taper as the internal surfaces 204 of the funnel. The external surfaces 208 of the funnel 200 at the braiding zone 206, however, also may include a taper that is less than the taper of the remaining portions of the external surfaces 208 of the funnel 200. The external surfaces 208 of the funnel 200 taper until an inflection point 214. At the inflection point 214, the external surfaces 208 may transition from a larger taper to less of a taper or where the external surfaces 208 may transition from a taper to substantially linear surfaces.

In certain instances, the funnel 200 is configured to facilitate arrangement of one or more fibers (that form a constraining mechanism) on the implantable medical device 104 for interlocking of the one or more fibers as discussed below with reference to FIG. 3. The inflection point 214 may serve as landing point for the one or more of the fibers, which may slide down the external surfaces 208 toward the exit point 212 of the funnel 200. As the implantable medical device 104 is forced through the exit point 212 of the funnel 200, the one or more fibers slide off the external surfaces 208 to engage the implantable medical device 104. In certain instances, the one or more fibers are engaged with the implantable medical device 104 under tension to maintain the implantable medical device 104 in the reduced diameter.

Figure 3B:
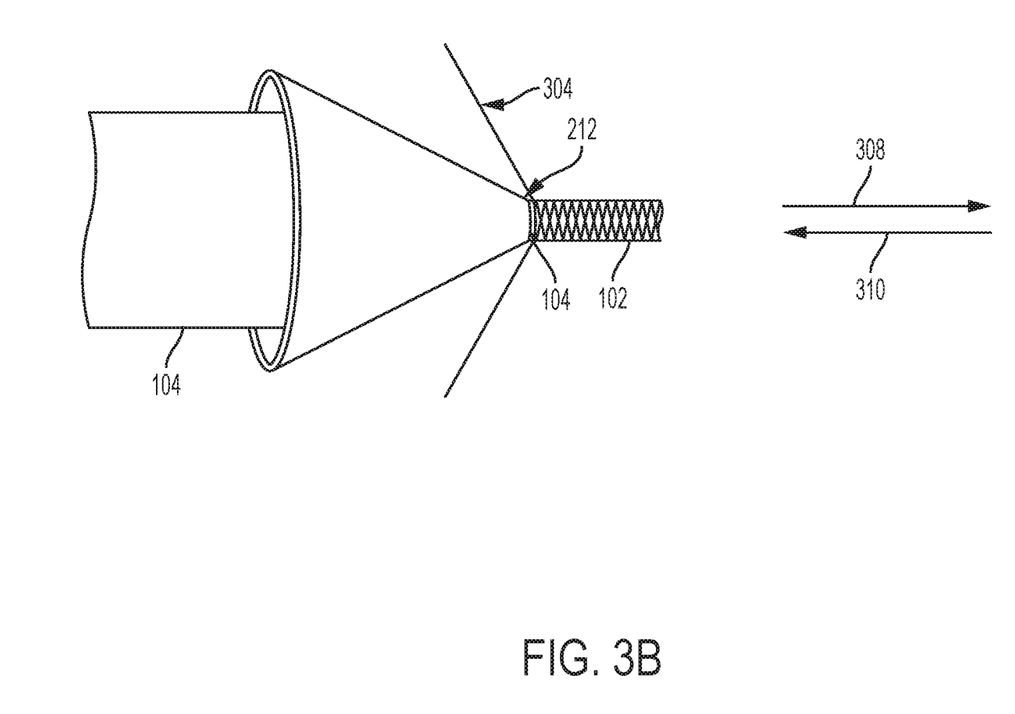
FIG. 3B is another example braider and implantable medical device according to some embodiments.

FIGS. 3A-B show an example funnel 200, constraining mechanism 102, and implantable medical device 104 according to some embodiments. The one or more fibers 304 may be arranged at an exit point 212 of a funnel 200 as shown in detail above with reference to FIG. 2. As shown in FIGS. 3A-3B, the implantable medical device 104 is in a reduced diameter or constrained configuration as it has exited a funnel 200. The funnel 200 may include a tapered outer profile at a distal end (e.g., as shown in FIG. 3A) or may include no outer taper (e.g., as shown in FIG. 3B). As shown in comparing FIGS. 3A and 3B, the funnel 200 shown in FIG. 3A includes an inflection point 214 and braiding zone 206, as discussed in further detail above with reference to FIGS. 2A-B while the funnel 200 shown in FIG. 3B does not include these aspects.

The braider 300 and the funnel 200 may form a system for forming a constraining mechanism for an implantable medical device delivery. In certain instances, the braider 300 is configured to interlock one or more fibers 304 along a length of the implantable medical device 104 while the implantable medical device 104 is in the reduced diameter to form the constraining mechanism. In addition, the one or more fibers 304 may be wrapped circumferentially about the implantable medical device 104.

In certain instances, the one or more fibers 304 are interlocked using one or more needles 306 (or other similar braiding structures such as elongate elements or instruments). The number of needles 306 may be equal to the number of fibers 304 used by the braider 300. In addition, the one or more fibers 304 interlocked together form a constraining mechanism 102. The constraining mechanism 102, as shown in FIG. 3, holds the implantable medical device 104 in the reduced configuration.

Certain prior constraining mechanisms that use fibers are knit or formed prior to being applied to or arranged about an implantable medical device. The prior constraining mechanisms are formed as a separate component and added as a separate step in a manufacturing process. In addition to the braider 300 (and funnel 200) reducing manufacturing steps by interlocking the one or fibers 304 directly on the implantable medical device 104 while the implantable medical device 104 is in the reduced diameter, forming the constraining mechanism 102 in this manner allows for a tighter constraint. Prior constraining mechanism, applied to a reduced diameter implantable medical device 104 after formation, may allow for the implantable medical device to expand while the prior constraining mechanism is arranged about the implantable medical device. Interlocking the one or more fibers 304 directly on the implantable medical device 104 minimizes the opportunity for expansion from the reduced diameter. The braider 300 and funnel 200 capture and constrain the implantable medical device 104 in its reduced diameter state. In certain instances, the device can exit the funnel 200 at an intermediate diameter and the application of the one or more fibers 304 may reduce the diameter to the target profile.

Figure 4:
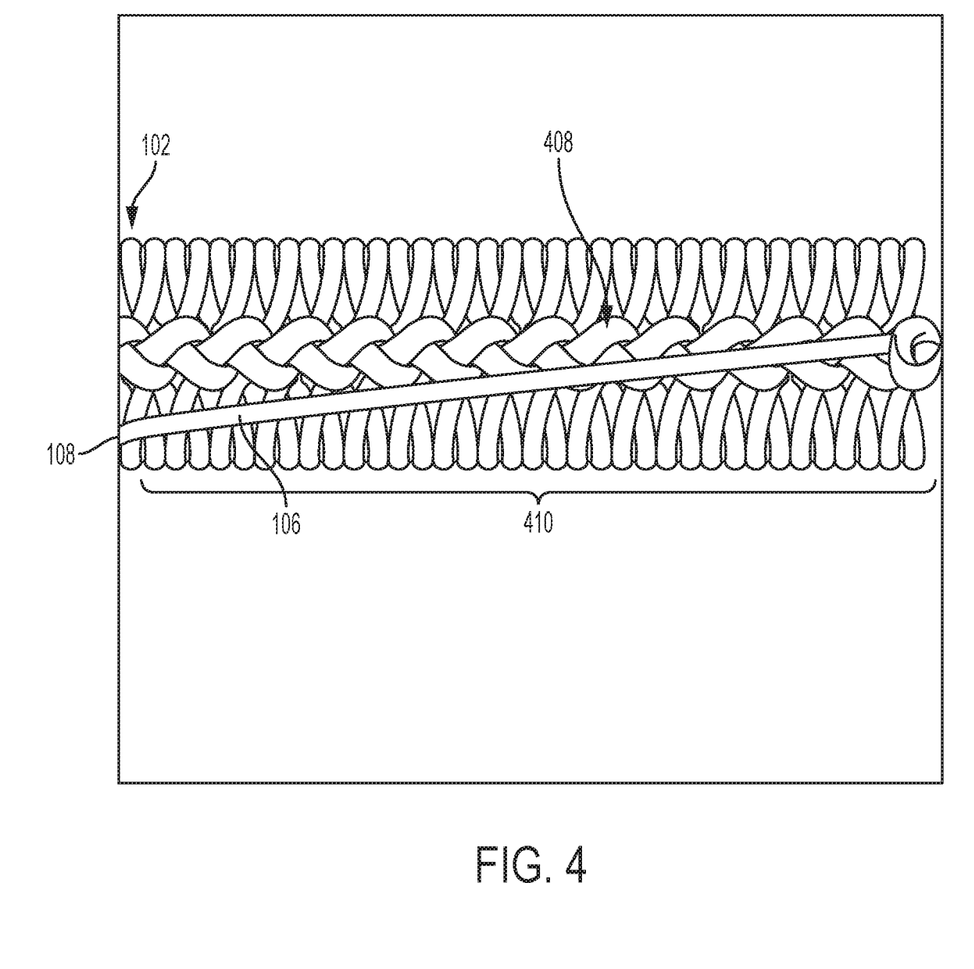
FIG. 4 is an example single fiber constraining mechanism according to some embodiments.
Figure 5:
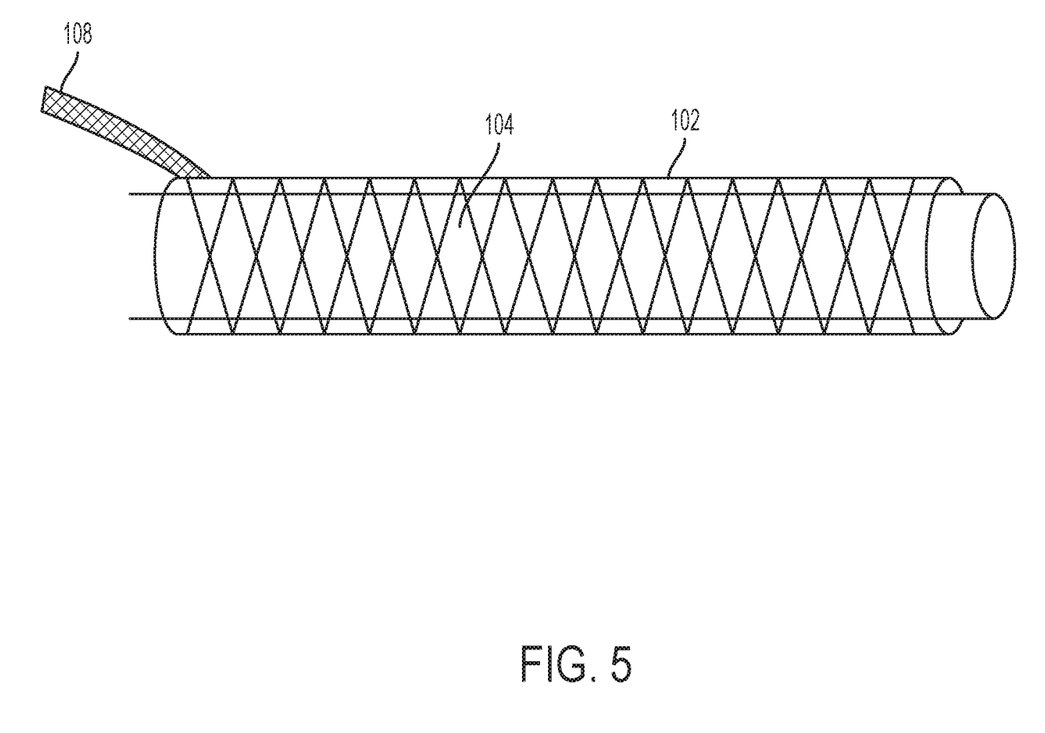
FIG. 5 is an example multi-fiber constraining mechanism according to some embodiments.

In certain instances, interlocking the one or more fibers 304 along the length of the implantable medical device 104 includes forming knots by knitting the one or more fibers 304 (e.g., as shown in FIG. 4). In other instances, interlocking the one or more fibers 304 along the length of the implantable medical device 104 includes braiding the one or more fibers 304 to form the constraining mechanism 102 (e.g., as shown in FIG. 5). The needles, (or fiber applicator), 306 may be automatically actuated to create the desired pattern for the constraining mechanism 102. The needles 306 may be move axially and/or rotated about the implantable medical device 104 to create knots, seams, or braids staggered about the circumference or the needles 306 may be maintained in a single location to create knots, seams, or braids that are aligned (e.g., as shown in FIG. 4).

In addition, the braider may interlock the one or more fibers 304 bidirectionally. For example, the braider may interlock the one or more fibers 304 in a first direction 308 to form a first layer of the constraining mechanism 102. The implantable medical device 104 may be forced into the braider, from the funnel 200, in the first direction 308 (shown in FIGS. 3A and 3B) to form the first layer of the constraining mechanism 102. In addition, the one or more fibers 304 may be wrapped circumferentially about the implantable medical device 104 after or during interlocking the one or more fibers 304. The braider 300 may interlock the one or more fibers 304 in a second direction 310 to form a second layer of the constraining mechanism 102. To form the second layer of the constraining mechanism 102, the implantable medical device 104 or the braider 300 is moved in the second direction 310.

In certain instances, the one or more fibers 304 may be interlocked together while the fibers 304 are in tension. The braider 300 may mechanically hold the one or more fibers 304 in tension during interlocking.

After the constraining mechanism 102 is formed, the implantable medical device 104 is maintained in the reduced diameter for delivery as noted above. Deploying the implantable medical device 104 is accomplished by pulling the end of one or more fibers 304 (as shown above with reference to FIG. 1) to release or un-knit the constraining mechanism 102.

FIG. 4 is an example single fiber constraining mechanism according to some embodiments. The constraining mechanism 102 may include a portion of a delivery system (e.g., a catheter and expandable medical device as shown in FIG. 1). FIG. 4 shows the constraining mechanism 102 in a constrained configuration in which an expandable medical device (not shown) is held to a diameter less than a deployed, expanded or working diameter. The constraining mechanism 102 is configured to constrain an expandable medical device to a delivery configuration. In addition, the constraining mechanism 102 includes a single fiber 106 arranged having a plurality of knots 408 to maintain the constraining mechanism 102 in a constrained configuration. The plurality of knots 408 are configured and arranged such that at least two of the plurality of knots 408 are in contact in the constrained configuration.

In certain instances, the single fiber 106 forms multiple loops 410 arranged circumferentially about the expandable medical device. In addition, and as shown in FIG. 4, the multiple loops 410 are packed at a density such that at least two of the multiple loops 410 are in physical contact. The loops 410 are unknotted portions of the single fiber 102 between knots of the plurality of knots 408.

The constraining mechanism 102 is arranged along a length of the expandable medical device. The constraining mechanism 102 is also circumferentially arranged about the expandable medical device and may substantially cover the expandable medical device 104 for delivery. The single fiber 106 may be arranged within a lumen (not shown) of the catheter and extend toward a proximal end of the catheter 100 that is arranged external to a patient during delivery of the expandable medical device. The one or more fibers 106 include a proximal end 108 that a user may apply tension to in order to release the constraining mechanism 102 and deploy the expandable medical device.

FIG. 5 is an example multi-fiber constraining mechanism 102 according to some embodiments. The multi-fiber constraining mechanism 102 may be formed by interlocking of multiple fibers together as discussed above with reference to FIGS. 2-3. Starting with two fibers, as many fibers as desired and appropriate can be combined in this manner, with the multi-fiber constraining mechanism 102 is formed by interlocking the fibers together.

The constraining mechanism 102 is arranged along a length of the expandable medical device 104. The constraining mechanism 102 is also circumferentially arranged about the expandable medical device 104 and may substantially cover the expandable medical device 104 for delivery. The single fiber 106 may be arranged within a lumen (not shown) of the catheter and extend toward a proximal end of the catheter 100 that is arranged external to a patient during delivery of the expandable medical device 104. The one or more fibers 106 include a proximal end 108 that a user may apply tension to in order to release the constraining mechanism 102 and deploy the expandable medical device 104.

The materials used to make the fiber or fibers of the present invention are likewise open to modification and customization for given applications. For most uses discussed herein the fiber or fibers used to form the constraining mechanism 102 may include: polytetrafluoroethylene (PTFE); expanded PTFE; silk; thermoplastic threads such as polypropylene; polyamide (nylon); various plastic or metal materials (e.g., stainless steel or nickel-titanium (nitinol) alloy); and bioresorbable materials, such as PLA or PGA. Particularly preferred for use in covering implantable medical devices are polytetrafluoroethylene (PTFE) threads, and especially expanded PTFE threads, such as threads available from W. L. Gore & Associates, Inc., Elkton, Md., under the trademark RASTEX® or sutures available from W. L. Gore & Associates, Inc., Flagstaff, Ariz., under the trademark GORE-TEX®.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A method of forming a constraining mechanism for an implantable medical device delivery, the method comprising:
reducing a diameter of the implantable medical device from a deployed diameter to a reduced diameter by forcing the implantable medical device through a funnel having internal surfaces reducing in diameter; and
wrapping one or more fibers circumferentially about the implantable medical device and the funnel, wherein the funnel includes a zone defining a landing position for the one or more fibers when forming the constraining mechanism, the zone having a length approximately equal to a length of the implantable medical device; and
interlocking the one or more fibers on the implantable medical device along a length of the implantable medical device while the implantable medical device is constrained by the funnel in the reduced diameter to form the constraining mechanism.

2. The method of claim 1, wherein interlocking the one or more fibers along the length of the implantable medical device includes knitting the one or more fibers to form the constraining mechanism.

3. The method of claim 1, wherein interlocking the one or more fibers along the length of the implantable medical device includes forming knots by knitting the one or more fibers.

4. The method of claim 1, wherein interlocking the one or more fibers includes knitting the one or more fibers together while the one or more fibers are in direct contact with the implantable medical device.

5. The method of claim 1, wherein interlocking the one or more fibers includes arranging the one or more fibers along the implantable medical device as the implantable medical device exits the funnel in the reduced diameter.

6. The method of claim 1, further comprising arranging the one or more fibers about an external surface of the funnel, and dragging the one or more fibers along the external surface of the funnel toward an end of the funnel where the implantable medical device exits the funnel in the reduced diameter to engage the implantable medical device.

7. The method of claim 1, wherein interlocking the one or more fibers occurs along the length of the implantable medical device in a first direction to form a first layer of the constraining mechanism, and further comprising interlocking the one or more fibers back onto the first layer along the length of the implantable medical device in a second direction to form a second layer of the constraining mechanism.

8. The method of claim 1, wherein interlocking the one or more fibers includes using a device to knit together the one or more fibers.

9. The method of claim 8, wherein the device includes one or more needles, and the one or more needles are equal to the one or more fibers, and interlocking the one or more fibers includes knitting together the one or more fibers by the one or more needles.

10. A system for forming a constraining mechanism for an implantable medical device delivery, the system comprising:
a funnel configured to reduce a diameter of the implantable medical device from a deployed diameter to a reduced diameter, wherein the funnel defines an exit point; and
a device positioned adjacent to the exit point of the funnel and configured to interlock one or more fibers along a length of the implantable medical device at a zone defining a landing position for the one or more fibers when forming the constraining mechanism, the device configured to interlock the one or more fibers at the exit point while the implantable medical device is constrained by the funnel in the reduced diameter to form the constraining mechanism.

11. The system of claim 10, wherein the funnel includes internal surfaces reducing an internal diameter of the funnel and, wherein the zone has a length approximately equal to a length of the implantable medical device.

12. The system of claim 10, wherein the device includes one or more needles, and the one or more needles are equal to the one or more fibers, and interlocking the one or more fibers includes knitting together the one or more fibers by the one or more needles.

13. The system of claim 10, wherein the funnel is configured to facilitate arrangement of the one or more fibers on the implantable medical device for interlocking of the one or more fibers.

14. A method comprising:
loading an implantable medical device into a funnel having internal surfaces reducing an internal diameter of the funnel and a zone defining a landing position for one or more fibers when forming a constraining mechanism;
reducing a diameter of the implantable medical device by forcing the implantable medical device through the internal surfaces reducing the internal diameter of the funnel; and
applying the one or more fibers to the implantable medical device while the implantable medical device is constrained by the funnel in the reduced diameter and as the implantable medical device exits the zone of the funnel to maintain the implantable medical device at reduced diameter.

15. The method of claim 14, wherein applying the one or more fibers includes knotting a single fiber together to form the constraining mechanism.

16. The method of claim 14, wherein applying the one or more fibers includes knitting together two or more fibers to form a constraining mechanism.

17. The method of claim 14, further comprising arranging the one or more fibers about an external surface of the funnel, and dragging the one or more fibers along the external surface of the funnel toward an end of the funnel where the implantable medical device exits the funnel in the reduced diameter to engage the implantable medical device.

18. The method of claim 14, wherein applying one or more fibers includes interlocking the one or more fibers occurs along the length of the implantable medical device in a first direction to form a first layer of the constraining mechanism, and further comprising interlocking the one or more fibers back onto the first layer along the length of the implantable medical device in a second direction to form a second layer of the constraining mechanism.

* * * * *